(12) United States Patent
Baptiste

(10) Patent No.: US 8,545,224 B2
(45) Date of Patent: Oct. 1, 2013

(54) METHOD FOR IMPROVING PRODUCTIVITY AND PERSONALIZATION FOR DENTAL PROSTHESES

(71) Applicant: David Baptiste, Westport, MA (US)

(72) Inventor: David Baptiste, Westport, MA (US)

(*) Notice: Subject to any disclaimer, the term of this patent is extended or adjusted under 35 U.S.C. 154(b) by 0 days.

(21) Appl. No.: 13/623,923

(22) Filed: Sep. 21, 2012

(65) Prior Publication Data

US 2013/0084542 A1  Apr. 4, 2013

Related U.S. Application Data

(62) Division of application No. 12/909,492, filed on Oct. 21, 2010.

(51) Int. Cl.
*A61C 13/10* (2006.01)

(52) U.S. Cl.
USPC ............................. 433/196; 433/171; 433/191

(58) Field of Classification Search
USPC ......... 433/167, 171–172, 177–178, 180–181, 433/199.1, 202.1, 204, 229, 191, 193–196, 433/213, 215, 218, 222.1, 223
See application file for complete search history.

(56) References Cited

U.S. PATENT DOCUMENTS

| | | | |
|---|---|---|---|
| 3,111,760 A * | 11/1963 | Semmelman et al. | 433/26 |
| 3,644,996 A | 2/1972 | Weinkle | |
| 3,921,292 A | 11/1975 | Ivchenko | |
| 4,337,042 A | 6/1982 | von Nostitz | |
| 4,470,815 A | 9/1984 | Hazar | |
| 4,533,325 A | 8/1985 | Blair et al. | |
| 4,705,476 A | 11/1987 | Blair | |
| 4,744,758 A | 5/1988 | Harrison et al. | |
| 5,951,291 A | 9/1999 | Albert et al. | |
| 6,079,981 A * | 6/2000 | Sekendur | 433/171 |
| 2006/0040234 A1 | 2/2006 | Posca | |
| 2008/0176189 A1* | 7/2008 | Stonisch | 433/215 |
| 2009/0233255 A1* | 9/2009 | De Souza Fonseca Silva et al. | 433/71 |

* cited by examiner

*Primary Examiner* — Cris L Rodriguez
*Assistant Examiner* — Edward Moran
(74) *Attorney, Agent, or Firm* — Salter & Michaelson

(57) ABSTRACT

A method for increasing the speed in setting artificial teeth in full dentures or dental prostheses. The method provides premade tooth segments, the premade tooth segments including at least one tooth that may be preset into a gingival roll manufactured with either the individual teeth connected together in the gingival roll or by a mid-tooth connection at the mesial and distal surfaces of each tooth in the segment. The method further includes setting the premade tooth segments into a wax bite rim and fitting the wax bite rim to the patient's mandibular or maxillary arch. Another aspect is a method for individualizing the denture or dental prosthesis whereby the incisors can be manipulated to create a personal and natural appearance.

15 Claims, 2 Drawing Sheets

METHOD FOR IMPROVING PRODUCTIVITY AND PERSONALIZATION FOR DENTAL PROSTHESES

BACKGROUND

The present disclosure relates generally to the setting of artificial teeth in full dentures (or dental prostheses) in order to improve the productivity in creating dentures and individualizing dentures to a particular patient.

Currently, dentures are conventionally made by inserting acrylic resin teeth or porcelain artificial teeth into a wax bite rim. A dental professional (e.g., dentist, dental technician, denturist or other dental team member) lines up the appropriate teeth and inserts the artificial teeth one by one into a wax bite rim. The dental professional then sculpts the wax around each tooth using an instrument, scalpel or blade to provide the appearance of a gum line. The sculpting provides individualization and creates a natural or realistic appearance to the denture. The process is then repeated for the complementary dental arch (maxillary or mandibular). Because the dental professional inserts each tooth one by one and then sculpts the ""gum line"" around the set teeth, this process is time consuming and takes a significant amount of skill and training.

Dental professionals have a need for a method which increases productivity and the ease of individualization of dentures to a particular patient. The speed at which a dental professional can create dentures can be increased by setting prefabricated tooth segments containing multiple teeth into a wax bite rim instead of setting single teeth one by one. The ease of individualization is increased as well by manipulating the appropriate tooth segments that will be visible in the mouth to create a natural appearance.

SUMMARY

The present invention (""Snap Tooth System"") provides a method of using pre-arranged segments of artificial teeth for the construction of full dentures. The dental professional will rapidly increase productivity, as well as provide a more personalized denture for each patient.

The present disclosure provides additional features, such as a method to individualize each segment. The reverse side of each individual segment is commonly referred to as the ridge lap area. In between each artificial tooth of any segment is referred to as the interproximal area. A channel is placed (interproximal area) in each segment to allow the dental professional to easily bend and ""SNAP THE SEGMENT APART"". This benefit allows the dental professional to individualize each tooth in the (""set-up"") arrangement, resulting in a more cosmetic looking denture.

The present disclosure provides a method for increasing the speed at which a dental professional can set artificial teeth in full dentures in occlusion. The present disclosure also provides a method for an easier way to individualize a full upper (maxillary) or full lower (mandibular) denture.

In an embodiment, the present disclosure provides a method of improving productivity of creating dentures in occlusion by setting artificial teeth onto a wax bite rim. This method comprises: (1) providing premade tooth segments manufactured with either the individual teeth connected together in the gingival area by a gingival roll, waxed bite rim or by a mid-tooth connection at the mesial and distal surfaces (the sides of a tooth) of each tooth in the segment; (2) setting the premade tooth segments into the wax bite rim; (3) fitting the wax bite rim to the patient's mandibular or maxillary arch; and (4) curing the completed denture. The gingival roll is the base of the tooth segment that is typically, but not always, a pinkish hue. The gingival roll is made out of acrylic resin or other similar material, including but not limited to acrylic resin, wax, silicone, composite, adhesive or the like, and simulates the gum line around the teeth. The acrylic resin or other similar material is typically a shade of pink to mimic the natural color of healthy gums. The reverse side of each individual segment is commonly referred to as the ridge-lap area. In between each artificial tooth of any segment is referred to as the interproximal area. A channel is placed (interproximal area) in each segment to allow the dental professional to easily bend and ""SNAP THE SEGMENT APART"". This benefit allows the dental professional to individualize each tooth in the (""set-up"") arrangement, resulting in a more cosmetic looking denture. These tooth segments allow for faster positioning into the wax bite rim than positioning tooth by tooth. The acrylic resin of the tooth segments additionally speeds the denture creation process by eliminating the time-consuming step of sculpting the gum line once the teeth have been set.

In another embodiment, the present disclosure provides a method of improving productivity of creating dentures in occlusion and individualizing the denture to a patient. This method comprises: (1) providing premade tooth segments for the anterior teeth wherein the premade tooth segments include a first tooth segment comprising at least one tooth, a second tooth segment comprising at least one tooth, a third tooth segment comprising at least one tooth with a first gingival roll, a fourth tooth segment comprising at least one tooth with a second gingival roll; (2) setting the premade tooth segments into a wax bite rim; (3) inserting artificial teeth into the posterior positions of the wax bite rim; (4) individualizing the dentures by manipulating the first, second, third, and fourth tooth segments appropriately to give the denture a unique and natural appearance; (5) fitting the wax bite rim to the patient's mandibular or maxillary arch; and (6) curing the completed denture. The gingival roll is the base of the tooth segment that is typically, but not always, a pinkish hue. The gingival roll is manufactured out of acrylic resin, composite or other similar material, including but not limited to acrylic resin, wax, silicone, composite, adhesive or the like, and simulates the gum line around the teeth. The acrylic resin or other similar material is typically a shade of pink to mimic the natural color of healthy gums. The method may also provide that the first tooth segment is comprised of the right-side canine (tooth #6 for maxillary arch or #27 for the mandibular arch being individual teeth with no gingival roll). The method may further provide that the second tooth segment is comprised of the left-side canine (tooth #11 for maxillary arch or #22 for the mandibular arch being individual teeth with no gingival roll). The method may even further provide that the third tooth segment is comprised of the right-side incisors (teeth #'s 7-8 for maxillary arch or #'s 25-26 for the mandibular arch). The method may also provide that the fourth tooth segment is comprised of the left-side incisors (teeth #'s 9-10 for maxillary arch or #'s 23-24 for the mandibular arch). The tooth segments are established so that individualizing the denture becomes particularly easy. For example, in the third tooth segment, the right-side central and lateral front teeth (incisors) are connected at Mid-tooth or have an acrylic resin gum line or gingival roll. In its complementary (fourth) tooth segment, the left-side central and lateral front teeth (incisors) are joined and have an acrylic resin gum line or gingival roll. The canines (first and second tooth segments) are presented as single teeth having no gingival roll. In addition, these four segments, the left and right incisors as well as the canines, can be manipulated easily as segments in the dental arch to individualize the denture. If also creating the mandibular arch, the same process applies for the lower incisor and canine segments. These prejoined segments allow the dental professional to more easily, and more quickly individualize a set of dentures in occlusion for a patient.

The upper (maxillary) arch posterior segment may be arranged in linear type occlusion or with a compensating curve (curve of spec) for continuous bilateral balanced occlusion. The linguals of a particular segment could be """"set"""" to a straight edge, which automatically provides the proper degree of buccal curvature.

In a further embodiment, the present disclosure provides a method of improving productivity of setting dentures in occlusion and individualizing a denture to a patient. This method comprises: (1) providing six premade tooth segments, wherein a first tooth segment comprising at least one tooth with a first gingival roll, a second tooth segment comprising at least one tooth with a second gingival roll, a third tooth segment comprising at least one tooth with a third gingival roll, a fourth tooth segment comprising at least one tooth with a fourth gingival roll, a fifth tooth segment comprising at least one tooth, a sixth tooth segment comprising at least one tooth; (2) setting the premade tooth segments into the wax bite rim; (3) individualizing the denture by manipulating the first, second, third, fourth, fifth, and sixth tooth segments appropriately to give the denture a unique and natural appearance; (4) fitting the wax bite rim to the patient's mandibular or maxillary arch; and (5) curing the denture. The gingival roll is manufactured out of acrylic resin or other similar material, including but not limited to acrylic resin, wax, silicone, composite, adhesive or the like, and simulates the gum line around the teeth. The acrylic resin or other similar material is typically a shade of pink to mimic the natural color of healthy gums. The method may also provide that the first tooth segment is comprised of the right-side molars and premolars (teeth #'s 2-5 for maxillary arch or #'s 28-31 for the mandibular arch). The method may further provide that the second tooth segment is comprised left-side molars and premolars (teeth #'s 12-15 for maxillary arch or #'s 18-21 for the mandibular arch). The method may also provide that the third tooth segment is comprised of the right-side incisors (teeth #'s 7-8 for maxillary arch or #'s 25-26 for the mandibular arch). The method may further provide that the fourth tooth segment is comprised of the left-side incisors (teeth #'s 9-10 for maxillary arch or #'s 23-24 for the mandibular arch). The method may even further provide that the fifth tooth segment is comprised of the right-side canine (tooth #6 for maxillary arch or #27 for the mandibular arch being individual teeth with no gingival roll). The method may further provide that the sixth tooth segment is comprised of the left-side canine (tooth #11 for maxillary arch or #22 for the mandibular arch being individual teeth with no gingival roll).

In a further embodiment, the present disclosure provides a method of improving productivity of setting dentures in occlusion and individualizing a denture to a patient. This method comprises: (1) providing six premade tooth segments, wherein a first tooth segment comprising at least one tooth with a first gingival roll, a second tooth segment comprising at least one tooth with a second gingival roll, a third tooth segment comprising at least one tooth with a third gingival roll, a fourth tooth segment comprising at least one tooth with a fourth gingival roll, a fifth tooth segment comprising at least one tooth, a sixth tooth segment comprising at least one tooth; (2) setting the premade tooth segments into a wax bite rim; (3) individualizing the denture by manipulating the first, second, third, fourth, fifth, and sixth tooth segments appropriately to give the denture a unique and natural appearance; (4) fitting the wax bite rim to the patient's mandibular or maxillary arch; and (5) curing the dental prosthesis. The gingival roll is manufactured out of acrylic resin or other similar material, including but not limited to acrylic resin, wax, silicone, composite, adhesive or the like, and simulates the gum line around the teeth. The acrylic resin or other similar material is typically a shade of pink to mimic the natural color of healthy gums. The method may also provide that the reverse side of each tooth segment (ridge-lap area) has channels in between (the interproximal region) each of the individual teeth. Moreover, the method may provide that the channels in between teeth allow the individual teeth to snap apart from the tooth segment in order to further individualize the tooth arrangement and characteristics in a specific tooth segment. The method may further provide that the first tooth segment is comprised of the right-side molars and premolars (teeth #'s 2-5 for maxillary arch or #'s 28-31 for the mandibular arch). The method may additionally provide that the second tooth segment is comprised left-side molars and premolars (teeth #'s 12-15 for maxillary arch or #'s 18-21 for the mandibular arch). The method may also provide that the third tooth segment is comprised of the right-side incisors (teeth #'s 7-8 for maxillary arch or #'s 25-26 for the mandibular arch). The method may further provide that the fourth tooth segment is comprised of the left-side incisors (teeth #'s 9-10 for maxillary arch or #'s 23-24 for the mandibular arch). The method may even further provide that the fifth tooth segment is comprised of the right-side canine (tooth #6 for maxillary arch or #27 for the mandibular arch being individual teeth with no gingival roll). The method may further provide that the sixth tooth segment is comprised of the left-side canine (tooth #11 for maxillary arch or #22 for the mandibular arch being individual teeth with no gingival roll).

By providing the dental professional with preset, premade artificial teeth with a gingival roll and interproximal channels on the ridge-lap areas of the tooth segments, both trained and untrained dental professionals will produce full dentures that are consistent in occlusion and quality in less time than if the teeth were positioned (""""set up"""") individually, and yet have an aesthetic appearance. Such dentures may also be created and retained in wax or a similar material for a patient's """"try-in stage."""" Moreover, the wax denture can be removed from the wax to change not only the appearance, but to also change the size, mould, or shade of the denture for the edentulous patient.

Additional features and advantages are described herein and will be apparent from the following Detailed Description and the figures.

DETAILED DESCRIPTION

Figure 1:
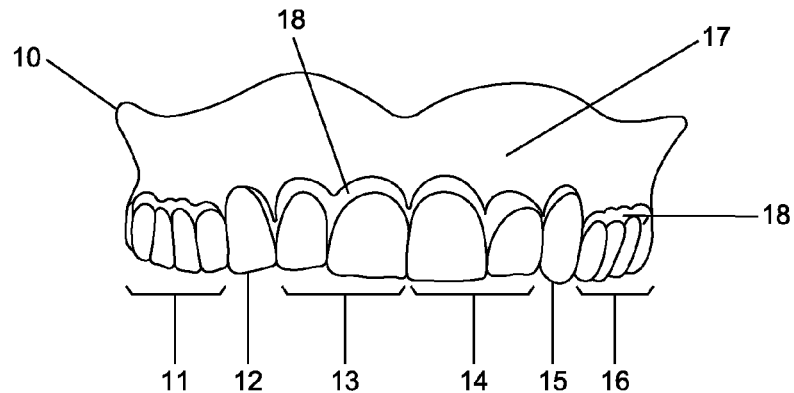
FIG. 1: complete maxillary arch with gingival rolls and wax bite rim.

Referring to FIG. 1, an embodiment of a complete prosthetic maxillary arch 10 is shown. The complete prosthetic maxillary arch 10 includes an upper right molar segment 11, an upper right canine with no gingival roll 12, an upper right incisor segment 13, an upper left incisor segment 14, an upper left canine with no gingival roll 15, and an upper left molar segment 16 secured to the maxillary wax bite rim 17. Tooth segments 11, 13, 14, and 16 include a gingival roll manufactured with either the individual teeth connected together in the gingival area by a gingival roll or by a mid-tooth 26 connection at the mesial and distal surfaces (the sides of a tooth) of each tooth in the segment 18. The tooth segments are secured to the wax bite rim 17 by curing the wax rim after setting the segments within.

In this embodiment, a dental professional can more quickly configure the complete prosthetic maxillary arch 10 because he or she is only working with six (6) tooth segments as opposed to fourteen (14) individual teeth. Additionally, the embodiment helps prevent the incorrect placement of a particular tooth due to the use of segments instead of individual teeth.

In the illustrated embodiment, the tooth segments 11, 13, 14, and 16 included in the complete prosthetic maxillary arch 10 each have a gingival roll 18 as part of the tooth segment. The gingival roll 18 provides the denture with a realistic appearance. The gingival roll 18 is manufactured out of acrylic resin or other similar material, including acrylic resin, wax, or the like, and simulates the gum line around the teeth. The acrylic resin or other similar material is typically a shade of pink to mimic the natural color of healthy gums. In addition, the gingival roll 18 also increases the speed at which a dental professional can complete a dental prosthesis.

Conventionally, after a dental professional has placed each individual tooth into its place in the wax rim, he or she must sculpt a proper gum line. Without this added gum line, the artificial teeth awkwardly protrude from the wax bite rim and have a skeletal appearance. Accordingly, a dental professional will use acrylic resin or other similar material, including but not limited to acrylic resin, wax, silicone, composite, adhesive or the like, to provide a proper gum line or gingival roll and create a realistic look to the denture. In order to produce a realistic effect, a dental professional must be highly skilled and the process is time consuming. It is an object of the current invention to speed up the process of creating a gum line or gingival roll without detracting from the accuracy or realism provided by a dental professional.

In an embodiment, the prejoined tooth segments 11, 13, 14, and 16 include a gingival roll 18 made of acrylic resin or other similar material. Typically, the material used is a shade of pink or colored pink to simulate healthy gums. Nevertheless, the material can be any color. The addition of the gingival roll 18 to the tooth segments replace the conventional step of creating a sculpting an original gum line for each denture thereby saving time and further preventing a mistake by the dental professional.

Figure 2:
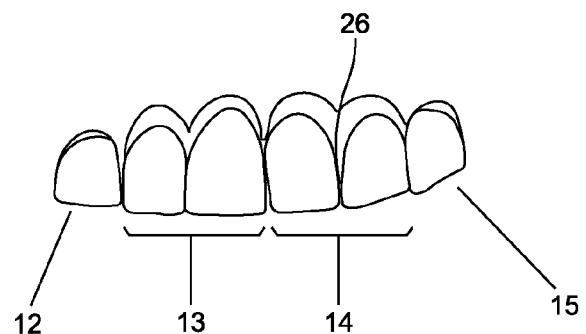
FIG. 2: upper right and upper left incisors with gingival rolls and upper right and upper left canines with no gingival rolls.

Referring to FIG. 2, an embodiment of the invention is shown incorporating upper right canine with no gingival roll 12, upper right incisor segment 13, upper left incisor segment 14, upper left canine with no gingival roll 15. By manipulating these tooth segments, a dental professional is able to individualize the maxillary arch denture to the specifications and characteristics of a particular patient. Conventionally, dental professionals set the six (6) front teeth individually into the wax bite rim. In addition, dental professionals set the teeth uniformly to simulate the appearance of ""perfect teeth."" However, perfect teeth may look fake or lack the character desired. Because the maxillary front teeth are the most visible, it is important that a patient have the ability to customize and individualize those teeth. Accordingly, an embodiment of the invention provides for the manipulation of the upper right canine with no gingival roll 12, upper right incisor segment 13, upper left incisor segment 14, upper left canine with no gingival roll 15 to individualize and give character to the denture. For example, a greater curve of the canines and incisors along the dental arch is typically more feminine while straighter, more rigid setting of the incisors and canines denote a more masculine appearance. In addition, using the incisor segments (maxillary or mandibular), a dental professional can provide as much or as little as a gap between the front teeth to mimic the person's real teeth. Alternatively, the dental professional can also partially overlap the incisor segments to provide a different natural look. Moreover, the tooth segments may be arranged in linear type occlusion or with a compensating curve (curve of spee) for continuous bilateral balanced occlusion. The linguals of a particular segment could be ""set"" to a straight edge, which automatically provides the proper degree of buccal curvature. Many other configurations are possible, left to the creativity and desire of the dental professional and the patient. Because the incisor segments are premade, such manipulation is relatively simple and takes far less time than the conventional method. This allows a patient to have a unique pair of dentures customized to his or her preference. This also humanizes the denture for both the patient and the world around him or her.

Figure 3:
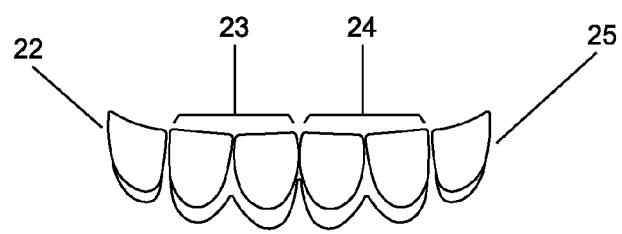
FIG. 3: lower right and lower left incisors teeth with gingival rolls.
Figure 4:
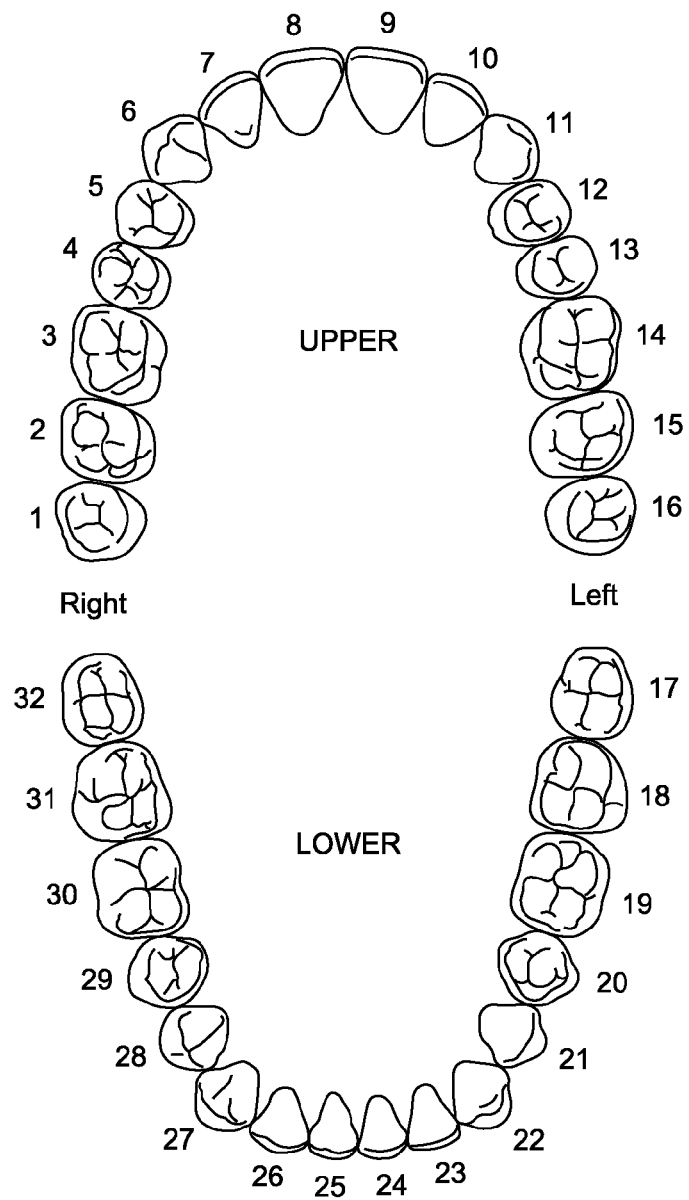
FIG. 4: complete numbered maxillary and mandibular arches.

Referring to FIG. 3, an embodiment of the invention is shown incorporating lower right canine with no gingival roll 22, lower right incisor segment 23, lower left incisor segment 24, lower left canine with no gingival roll 25. While not as visible as the maxillary front teeth, patients may also desire customization and individualization of the mandibular front teeth. This customization is achieved in the same way customization of the maxillary front teeth is achieved.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method for creating dentures or dental prostheses by setting artificial teeth in a wax bite rim, the method comprising:

providing a plurality of premade artificial tooth segments for forming at least a part of a prosthetic arch, the premade artificial tooth segments having at least one tooth in each segment, some of the premade artificial tooth segments having more than one tooth, and at least some of the artificial tooth segments having a gingival roll at a base thereof;

wherein the step of providing includes including manufacturing the individual artificial teeth of a premade artificial tooth segment connected together by a mid-tooth connection at the mesial and distal surfaces of adjacent teeth of the premade artificial tooth segment;

wherein the mid tooth connection forms a channel on the reverse side of the teeth on the mesial distal surfaces between the adjacent teeth in the artificial tooth segment;

bending and snapping apart at least one tooth from an artificial tooth segment having more than one tooth at the channel in order to separate and individualize the tooth arrangement and characteristics of the teeth;

setting the premade tooth segments, including the snapped apart at least one tooth, into the wax bite rim; and fitting the wax bite rim to the dental arch of a patient and curing the wax bite rim.

2. The method of claim 1 where the dental arch is one of a maxillary arch and a mandibular arch.

3. The method of claim 1 where the gingival roll is one of acrylic resin, wax, silicone, adhesive, and composite.

4. The method of claim 1 where the gingival roll is a pinkish hue or a clear hue.

5. A method for creating dentures or dental prostheses and individualizing the dentures or dental prostheses to a patient by setting teeth in a wax bite rim, the method comprising:
   providing premade artificial tooth segments for anterior teeth wherein the premade artificial tooth segments include a first tooth segment having at least one tooth, a second tooth segment having at least one tooth, a third tooth segment having at least one tooth with a first gingival roll, a fourth tooth segment having at least one tooth with a second gingival roll;
   at least some of the tooth segments having more than one tooth;
   wherein the step of providing the premade artificial tooth segments includes providing a mid-tooth connection on the mesial and distal surfaces of two adjacent teeth in a tooth segment, which connects them together and forms a channel on the reverse side of the teeth in the interproximal area between the teeth;
   individualizing the denture by manipulating the first, second, third, and fourth tooth segments appropriately to give the denture a unique and natural appearance;
   bending and snapping apart a tooth from an artificial tooth segment at the channel allowing for separation and individualization in order to individualize the tooth arrangement and characteristics of the teeth;
   setting all the pre-made tooth segments and snapped apart tooth into a wax bite rim;
   fitting the wax bite rim to the patient's dental arch and curing the wax bite rim.

6. The method of claim 5 where the dental arch is one of a maxillary arch and a mandibular arch.

7. The method of claim 5 where the gingival roll is one of acrylic resin, wax, silicone, adhesive, and composite.

8. The method of claim 5 where the gingival roll is a pinkish hue or a clear hue.

9. The method of claim 5 wherein the first tooth segment is comprised of one of the right-side incisors, left-side incisors, right-side canine, and left-side canine.

10. A method for setting dentures or dental prostheses and individualizing a denture or dental prosthesis to a patient by setting teeth in a wax bite rim, the method comprising:
    providing six premade artificial tooth segments: a first tooth segment having at least one tooth with a first gingival roll, a second tooth segment having at least one tooth with a second gingival roll, a third tooth segment having at least one tooth with a third gingival roll, a fourth tooth segment having at least one tooth with a fourth gingival roll, a fifth tooth segment having at least one tooth, a sixth tooth segment having at least one tooth;
    at least some of the tooth segments having more than one tooth;
    wherein the step of providing the premade artificial tooth segments includes providing a mid-tooth connection on the mesial and distal surfaces of two adjacent teeth in a tooth segment which connects them together and forms a channel on the reverse side of the teeth in the interproximal area between the teeth;
    individualizing the denture by manipulating the first, second, third, fourth, fifth, and sixth tooth segments appropriately to give the denture a unique and natural appearance;
    bending and snapping apart a tooth from an artificial tooth segment at the channel allowing for separation and individualization in order to individualize the tooth arrangement and characteristics of the teeth;
    setting all the pre-made tooth segments and snapped apart tooth into a wax bite rim;
    fitting the wax bite rim to the patient's dental arch; and curing the wax bite rim.

11. The method of claim 10 where the dental arch is one of a maxillary arch and a mandibular arch.

12. The method of claim 10 where each gingival roll is acrylic resin.

13. The method of claim 10 where each gingival roll is one of wax, silicone, adhesive, and composite.

14. The method of claim 10 where each gingival roll is a pinkish hue or a clear hue.

15. The method of claim 10 wherein the first tooth segment comprises one of the right-side molars and premolars, left-side molars and premolars, right-side incisors, left-side incisors, right-side canine, and left-side canine.

* * * * *